United States Patent
Shimohata (10) Patent No.: US 10,742,856 B2
(45) Date of Patent: Aug. 11, 2020

(54) OPTICAL UNIT FOR ENDOSCOPE, ENDOSCOPE AND METHOD FOR MANUFACTURING OPTICAL UNIT FOR ENDOSCOPE

(71) Applicant: OLYMPUS CORPORATION, Tokyo (JP)

(72) Inventor: Takahiro Shimohata, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/188,488

(22) Filed: Nov. 13, 2018

(65) Prior Publication Data

US 2019/0076002 A1    Mar. 14, 2019

Related U.S. Application Data

(63) Continuation of application No. PCT/JP2016/065280, filed on May 24, 2016.

(51) Int. Cl.
| | |
|---|---|
| *H04N 5/225* | (2006.01) |
| *A61B 1/04* | (2006.01) |
| *A61B 1/00* | (2006.01) |
| *H01L 27/14* | (2006.01) |
| *G02B 7/02* | (2006.01) |
| *G02B 23/26* | (2006.01) *A61B 1/05* |
| (2006.01) | *H01L 27/146* |
| (2006.01) | |

(52) U.S. Cl.
CPC .............. *H04N 5/2254* (2013.01); *A61B 1/00* (2013.01); *A61B 1/0011* (2013.01);
(Continued)

(58) Field of Classification Search
CPC ................ H04N 5/2254; H04N 5/225; H04N 2005/2255; A61B 1/04; A61B 1/00;
(Continued)

(56) References Cited

U.S. PATENT DOCUMENTS

| | | | |
|---|---|---|---|
| 8,711,483 B2* | 4/2014 | Matsuno .......... | B29D 11/00307 359/620 |
| 2009/0244259 A1* | 10/2009 | Kojima ................ | H04N 5/2251 348/45 |

(Continued)

FOREIGN PATENT DOCUMENTS

| | | |
|---|---|---|
| EP | 2 157 782 A2 | 2/2010 |
| EP | 2 466 341 A1 | 6/2012 |

(Continued)

OTHER PUBLICATIONS

International Search Report dated Aug. 16, 2016 issued in International Application No. PCT/JP2016/065280.

*Primary Examiner* — Albert H Cutler
(74) *Attorney, Agent, or Firm* — Scully, Scott, Murphy & Presser, P.C.

(57) ABSTRACT

A lens unit includes a plurality of optical elements stacked, each of the plurality of optical elements including a glass substrate as a base, the glass substrates having a same size in respective cross-sections in a direction orthogonal to an optical path, and the optical elements are lens elements with resin lenses disposed on the respective bases, and each of the plurality of optical elements includes an annular recess portion surrounding the optical path and extending through the glass substrate, and a light shielding wall made of a light shielding material charged in the recess portion.

5 Claims, 11 Drawing Sheets (52) U.S. Cl.
CPC ...... *A61B 1/00096* (2013.01); *A61B 1/00163* (2013.01); *A61B 1/04* (2013.01); *A61B 1/051* (2013.01); *G02B 7/02* (2013.01); *G02B 7/021* (2013.01); *G02B 23/26* (2013.01); *H01L 27/14* (2013.01); *H01L 27/14623* (2013.01); *H01L 27/14627* (2013.01); *H01L 27/14685* (2013.01); *H01L 27/14687* (2013.01); *H04N 5/225* (2013.01)

(58) Field of Classification Search
CPC .............. A61B 1/00096; A61B 1/0011; A61B 1/00163; A61B 1/051; A61B 1/05; A61B 1/053; H01L 27/14; H01L 27/14623; H01L 27/14627; H01L 27/14685; H01L 27/14687; G02B 7/02; G02B 23/26; G02B 7/021; G02B 23/243; G06T 2207/10068
See application file for complete search history.

(56) References Cited

U.S. PATENT DOCUMENTS

| | | |
|---|---|---|
| 2010/0033647 A1 | 2/2010 | Okita et al. |
| 2010/0045845 A1 | 2/2010 | Yoneyama |
| 2010/0052192 A1 | 3/2010 | Hasegawa et al. |
| 2010/0117176 A1 | 5/2010 | Uekawa |
| 2012/0134028 A1* | 5/2012 | Maruyama ........... G02B 3/0031 359/601 |
| 2013/0286282 A1* | 10/2013 | Yamamoto ........... H04N 5/2257 348/374 |
| 2014/0246566 A1 | 9/2014 | Maruyama |

FOREIGN PATENT DOCUMENTS

| | | |
|---|---|---|
| EP | 2 682 797 A1 | 1/2014 |
| JP | 2009-240634 A | 10/2009 |
| JP | 2010-045463 A | 2/2010 |
| JP | 2010-048993 A | 3/2010 |
| JP | 2010-056170 A | 3/2010 |
| JP | 2010-118397 A | 5/2010 |
| JP | 2011-059678 A | 3/2011 |
| JP | 2011-081352 A | 4/2011 |
| JP | 2011-081353 A | 4/2011 |
| JP | 2011-081354 A | 4/2011 |
| JP | 2012-018993 A | 1/2012 |
| JP | 2013-125059 A | 6/2013 |
| JP | 5401628 B2 | 1/2014 |
| JP | 2014-056127 A | 3/2014 |
| WO | 2011/019067 A1 | 2/2011 |
| WO | 2012/117986 A1 | 9/2012 |

* cited by examiner

FIG. 16

OPTICAL UNIT FOR ENDOSCOPE, ENDOSCOPE AND METHOD FOR MANUFACTURING OPTICAL UNIT FOR ENDOSCOPE

CROSS REFERENCE TO RELATED APPLICATION

This application is a continuation application of PCT/JP2016/065280 filed on May 24, 2016, the entire contents of which are incorporated herein by this reference.

BACKGROUND OF THE INVENTION

Field of the Invention

The present invention relates to an optical unit for endoscope, the optical unit being disposed in a rigid distal end portion of an endoscope and including a plurality of elements stacked, an endoscope including an optical unit for endoscope disposed in a rigid distal end portion, the optical unit including a plurality of elements stacked, and a method for manufacturing an optical unit for endoscope, the optical unit being disposed in a rigid distal end portion of an endoscope and including a plurality of elements stacked.

Description of the Related Art

For alleviating invasiveness, it is important to make an optical unit for endoscope to be disposed in a rigid distal end portion of an endoscope thinner. As a method for efficiently manufacturing a thin optical unit, a method exists in which a bonded wafer is fabricated by stacking element wafers each including a plurality of optical elements and the bonded wafer is cut into individual wafer-level stacks.

Japanese Patent Application Laid-Open Publication No. 2012-18993 discloses an image pickup module including a wafer-level stack. The image pickup module is fabricated by bonding a lens wafer including a plurality of lenses and an image pickup wafer including a plurality of image pickup devices to each other and then cutting the resulting wafer into individual pieces.

SUMMARY OF THE INVENTION

An optical unit for endoscope according to an embodiment of the present invention includes a plurality of optical elements stacked, each of the plurality of optical elements including a glass substrate as a base, the glass substrates having a same size in respective cross-sections in a direction orthogonal to an optical path, and at least any one of the optical elements is a lens element including a resin lens disposed on the base, and each of the optical elements includes an annular recess portion surrounding the optical path and extending through the glass substrate, and a light shielding wall made of a light shielding material charged in the recess portion.

An endoscope according to another embodiment includes an optical unit for endoscope in a rigid distal end portion of an insertion portion, and the optical unit for endoscope includes a plurality of optical elements stacked, each of the plurality of optical elements including a glass substrate as a base, the glass substrates having a same size in respective cross-sections in a direction orthogonal to an optical path, and at least any one of the optical elements is a lens element including a resin lens disposed on the base, and each of the optical elements includes an annular recess portion surrounding the optical path and extending through the glass substrate, and a light shielding wall made of a light shielding material charged in the recess portion.

A method for manufacturing an optical unit for endoscope according to another embodiment includes: a step of forming a plurality of annular through recess portions in each of a plurality of glass wafers; a step of fabricating light shielding walls by charging a light shielding material into the recess portions; a step of fabricating a bonded wafer by stacking the plurality of glass wafers with the light shielding walls fabricated; and a step of cutting the bonded wafer into individual optical units for endoscope, each including a plurality of optical elements stacked, each of the plurality of optical elements including a glass substrate as a base, the glass substrates having a same size in respective cross-sections in a direction orthogonal to an optical path, the plurality of optical elements including the respective light shielding walls surrounding the optical path, and the method further includes a step of disposing resin lenses inside respective recess portion formation areas of at least any one of the glass wafers before the step of fabricating a bonded wafer.

DETAILED DESCRIPTION OF THE PREFERRED EMBODIMENT(S)

First Embodiment

Figure 1:
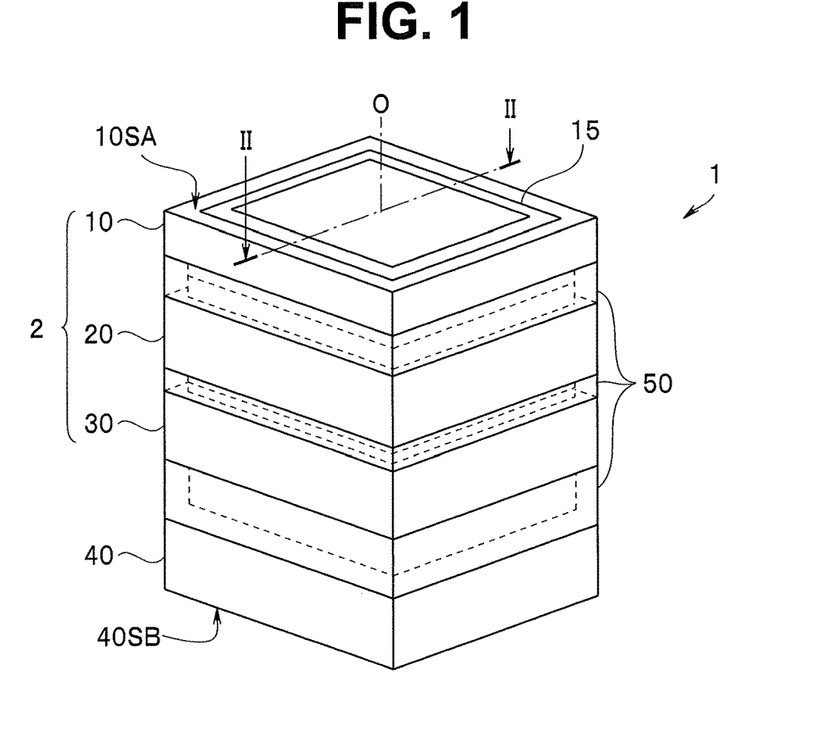
FIG. 1 is a perspective view of an optical unit for endoscope according to a first embodiment.
Figure 2:
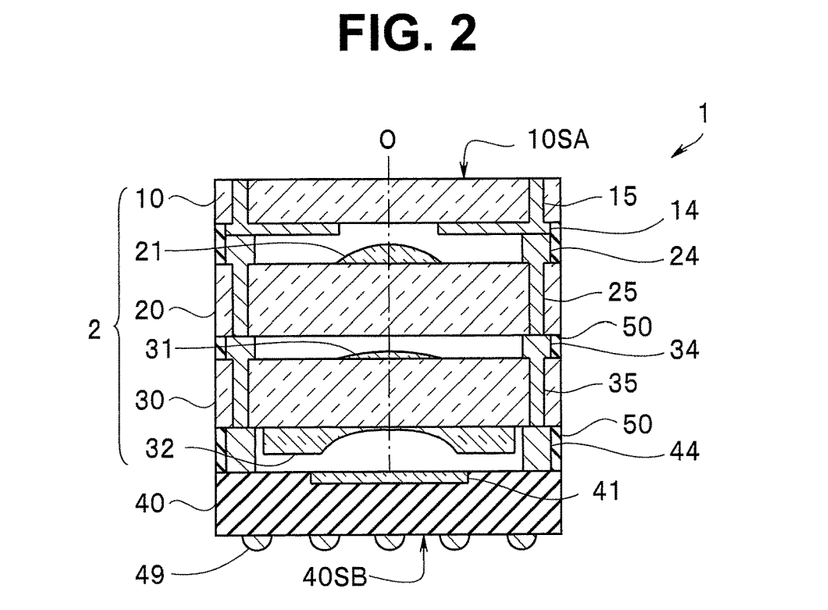
FIG. 2 is a cross-sectional view of the optical unit for endoscope according to the first embodiment along line II-II in FIG. 1.
Figure 3:
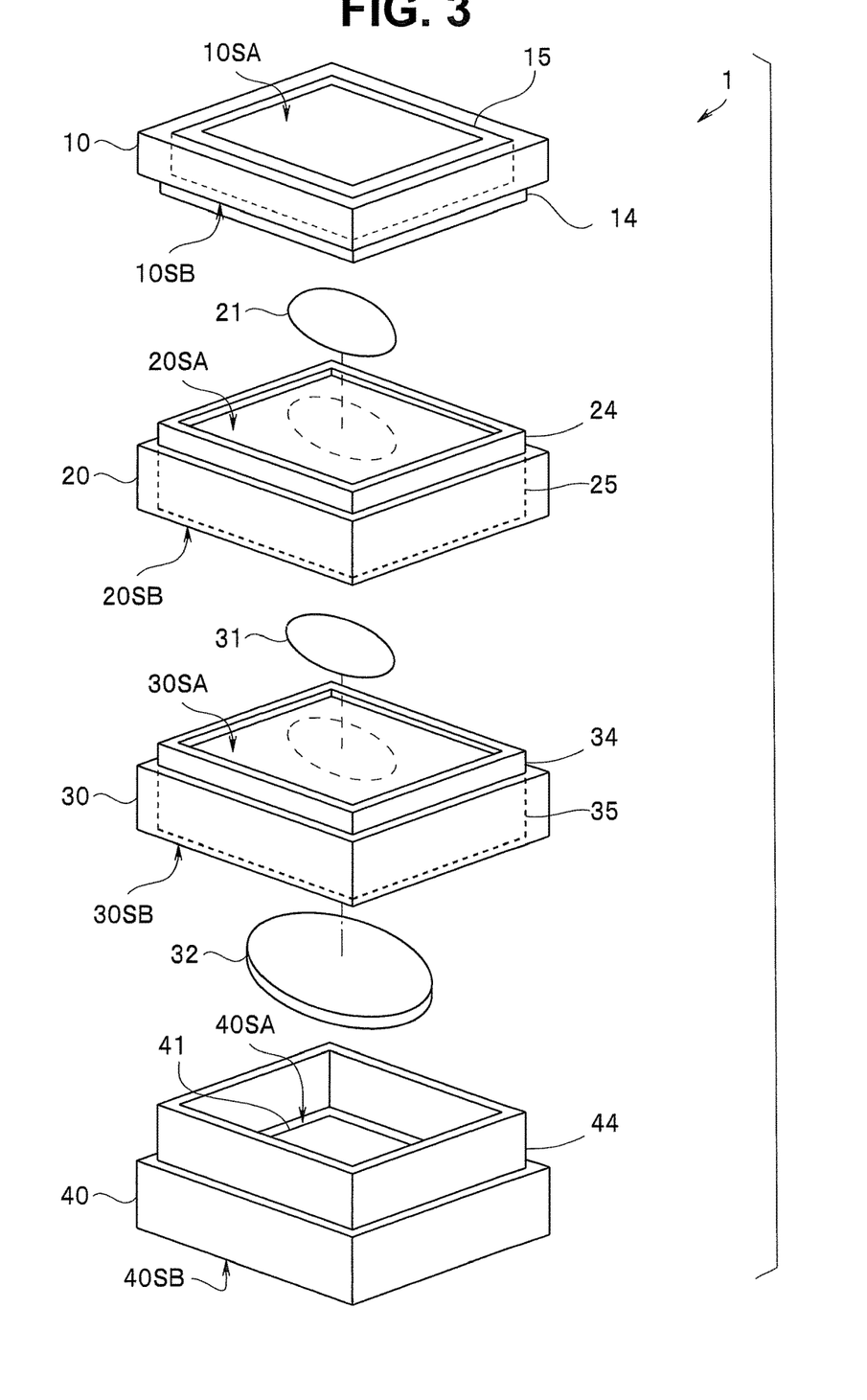
FIG. 3 is an exploded view of the optical unit for endoscope according to the first embodiment.

As illustrated in FIGS. 1 to 3, an optical unit for endoscope according to the present embodiment is a lens unit 2 including a plurality of optical elements 10 to 30 (10, 20, 30) stacked. The lens unit 2 forms an image pickup unit 1, which is an optical unit for endoscope according to another embodiment, jointly with an image pickup device 40.

In the following description, it should be understood that the drawings based on the respective embodiments are schematic ones, e.g., a relationship between a thickness and a width of each part and thickness ratios and relative angles among the respective parts are different from actual ones, and parts that are different in dimensional relationship and ratio depending on the drawings may be included in the drawing. Furthermore, illustration of some components may be omitted.

In the lens unit 2, the plurality of optical elements 10 to 30 each including a parallel plate glass substrate, as a base, is stacked. The parallel plate glass substrates have a same size in respective cross-sections in an optical path orthogonal direction, that is, a direction orthogonal to an optical axis O. The plurality of optical elements 10 to 30 are rectangular parallelepipeds and have a same size in respective cross-sections, and thus the lens unit 2 is a rectangular parallelepiped.

The optical element 10 is an infrared cut filter element having a function that blocks infrared light, and on a back face 10SB of the optical element 10, the back face 10SB facing a light entrance surface 10SA, a diaphragm 14, which is an optical diaphragm (diaphragm portion) for blocking a part of an optical path to adjust an amount of light, is disposed.

The optical element 20 is a hybrid lens element made of plastic and glass, in which an aspherical convex lens 21 made of a resin is disposed on a first principal surface 20SA of the relevant parallel plate glass substrate. The optical element 30 is a hybrid lens element in which an aspherical convex lens 31 made of a resin is disposed on a third principal surface 30SA of the relevant parallel plate glass substrate and an aspherical concave lens 32 made of a resin is disposed on a fourth principal surface 30SB facing the third principal surface 30SA.

In other words, from among the optical elements 10 to 30 of the lens unit 2, each of optical elements 20, 30 is a lens element in which resin lens(es) are disposed on the relevant base.

Then, the optical elements 10 to 30 include respective through holes (rings) which are annular continuous recess portions surrounding the optical path, and respective light shielding walls 15 to 35 (15, 25, 35) made of copper, which is a light shielding material, the copper being charged in the respective through holes. The light shielding walls 15 to 35 of the optical elements 10 to 30 have a frame-like shape and a same size in respective cross-sections surrounding the optical path, and surround the optical path with no discontinuation.

Also, the annular diaphragm 14 is provided so as to extend in a projecting manner from the light shielding wall 15 in the back face 10SB of the optical element 10. An outer periphery of the diaphragm 14 has a rectangular shape, but an inner periphery of the diaphragm 14 has a round shape. In other words, a center of the diaphragm 14 is a round space.

An annular spacer 24 is provided so as to extend in a projecting manner from the light shielding wall 25 in the first principal surface 20SA of the optical element 20. The spacer 24 comes into contact with the diaphragm 14. A distance between the two adjacent optical elements 10 and 20, that is, a distance between the back face 10SB of the optical element 10 and the first principal surface 20SA of the optical element 20 is defined by a thickness of the diaphragm 14 and a thickness of the spacer 24.

The annular spacer 34 is provided so as to extend in a projecting manner from the light shielding wall 35 in the third principal surface 30SA of the optical element 30. The spacer 34 comes into contact with a second principal surface 20SB of the optical element 20. A distance between the two adjacent optical elements 20 and 30, in other words, a distance between the second principal surface 20SB of the optical element 20 and the third principal surface 30SA of the optical element 30 is defined by a thickness of the spacer 34.

Also, a sealing resin 50 is charged in an outer peripheral portion of each of the spacers 14, 24, 34 for enhancing bonding strength and reliability.

In the lens unit 2, an entry of external light into the optical path is blocked by the annular light shielding walls 15, 25, 35, the annular diaphragm 14 and the annular spacers 24, 34.

The lens unit 2 having a light shielding function has no need to dispose a light shielding film on an outer face or provide a lens barrel having a light shielding function and thus is thin. Also, as described later, the light shielding walls 15, 25, 35 are fabricated in a wafer process, and thus, the lens unit 2 is easy to manufacture. Furthermore, the lens unit 2 includes the diaphragm 14 and the spacer 24, 34 provided so as to extend from the respective light shielding walls 15, 25, 35 and thus is further easy to manufacture.

On the other hand, in an image pickup surface 40SA of the image pickup device 40 including a semiconductor substrate, a light receiving section 41 such as a CMOS light receiving element, and an annular spacer 44 are disposed. The light receiving section 41 receives light collected by the optical elements 10, 20, 30 of the lens unit 2. The annular spacer 44 comes into contact with the fourth principal surface 30SB of the optical element 30. In other words, a distance between the fourth principal surface 30SB of the optical element 30 and the image pickup surface 40SA of the image pickup device 40 is defined by a thickness of the spacer 44. The light receiving section 41 is connected to external connection electrodes 49 on the back face 40SB via non-illustrated through wiring.

A cross-section in the optical path orthogonal direction of the image pickup device 40 has a rectangular shape of a size that is the same as the size of the optical elements 10 to 30 of the lens unit 2. Thus, the image pickup unit 1 having a light shielding function is a thin rectangular parallelepiped and is easy to manufacture.

<Endoscope>

Figure 4:
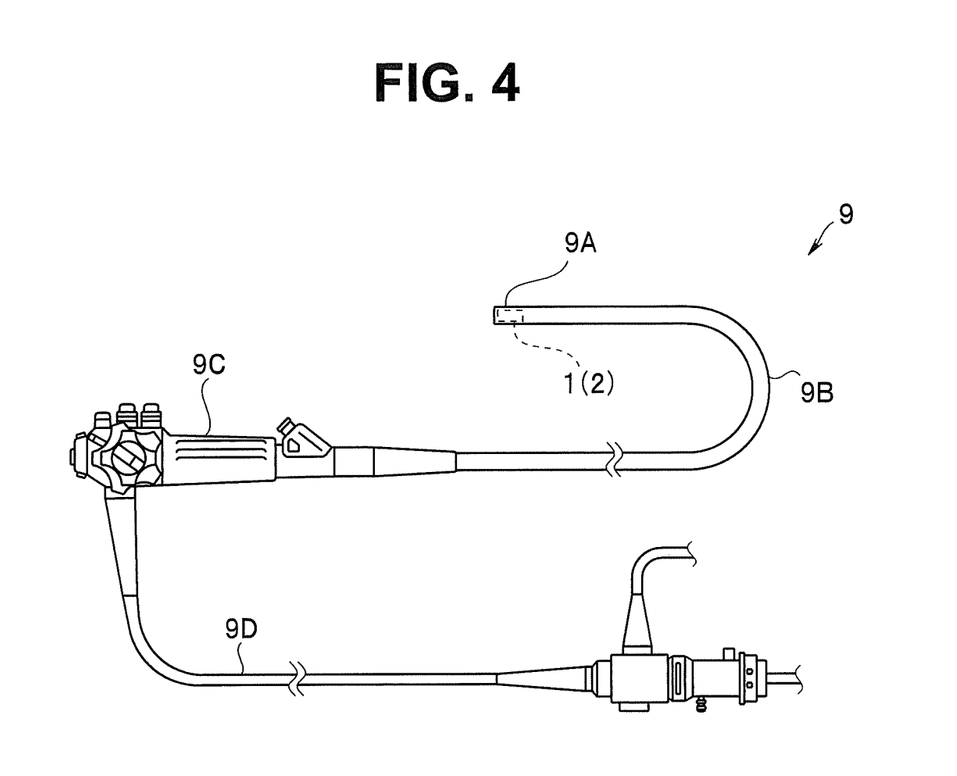
FIG. 4 is a diagram of an outer appearance of an endoscope including the optical unit for endoscope according to the first embodiment.

As illustrated in FIG. 3, the image pickup unit 1 (lens unit 2), which is disposed in a rigid distal end portion 9A of an insertion portion 9B of an endoscope 9, picks up an object image and processes and outputs an image pickup signal. In other words, an endoscope 9 according to another embodiment includes an insertion portion 9B including the image pickup unit 1 disposed in the rigid distal end portion 9A, an operation portion 9C disposed on the proximal end side of the insertion portion 9B, and a universal cord 9D extending from the operation portion 9C. An image pickup signal outputted from the image pickup unit 1 disposed in the rigid distal end portion 9A is transmitted to a processor via a cable inserted through the universal cord 9D. Also, a drive signal is transmitted from the processor to the image pickup unit 1 via a cable inserted through the universal cord 9D.

The endoscope 9 according to the other embodiment includes the image pickup unit 1 (lens unit 2) having a light shielding function in the rigid distal end portion 9A and thus is thin and easy to manufacture.

<Manufacturing Method>

Next, a method for manufacturing the image pickup unit 1 (lens unit 2) will be described with reference to the flowchart illustrated in FIG. 5. Also, FIGS. 6A to 6E indicate respective steps of manufacturing an element wafer 20W as an example of a method for manufacturing an element wafer.

<Step S11> Resin Lens Disposition

Figure 7:
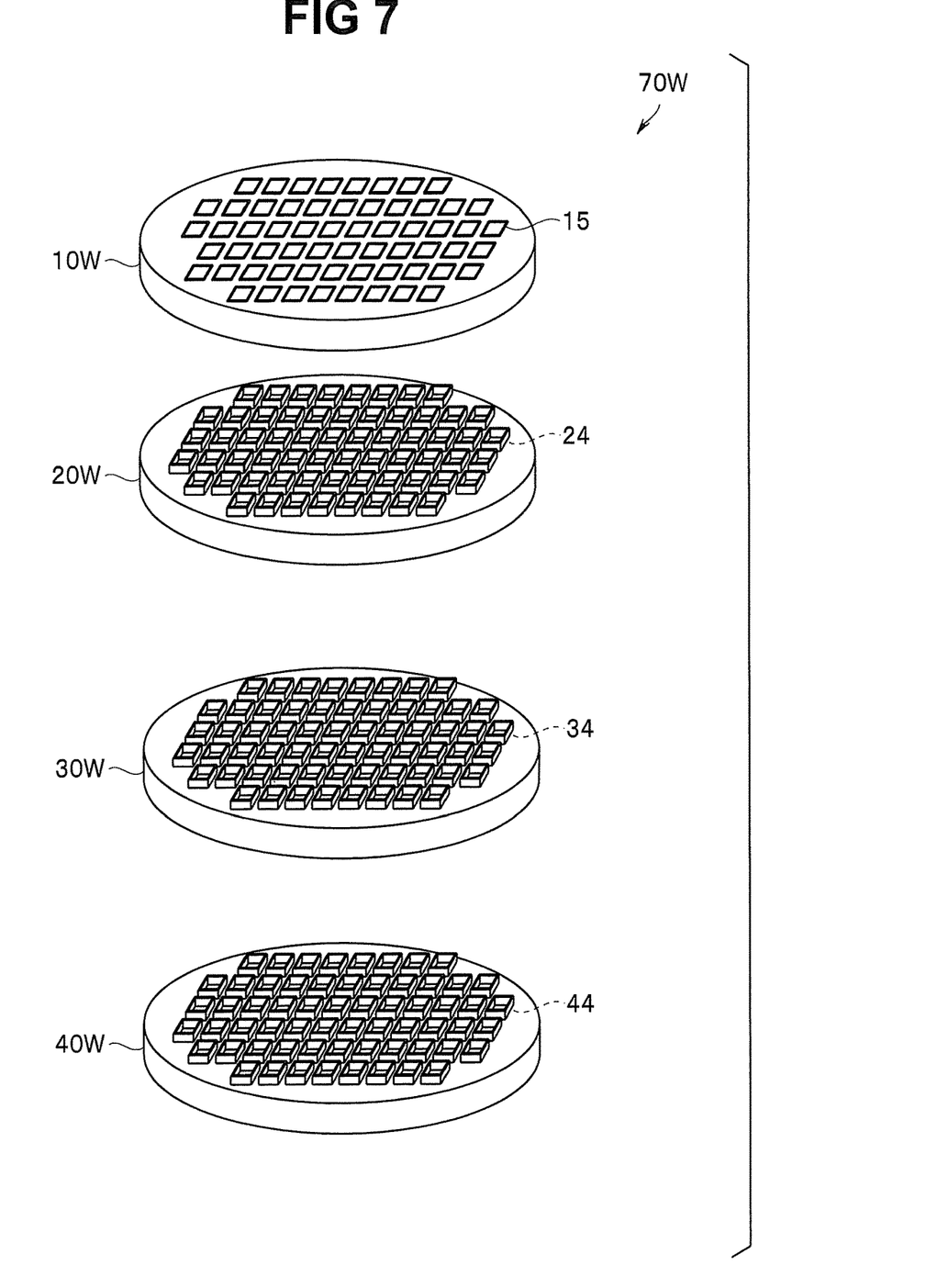
FIG. 7 is an exploded view of a bonded wafer for describing the method for manufacturing the optical unit for endoscope according to the first embodiment.

A plurality of parallel plate glass wafers 10W to 30W (10W, 20W, 30W, see FIG. 7) are prepared. Each of the glass wafers 10W to 30W is, e.g., a light-transmissive, for example, transparent and colorless, glass wafer or a glass filter wafer configured to block light in a predetermined wavelength band. Respective thicknesses of the glass wafers 10W to 30W are determined according to respective required optical characteristics. As described later, the glass wafers 10W to 30W are cut into glass substrates 10 to 30 of respective lens units 2.

Figure 6A:
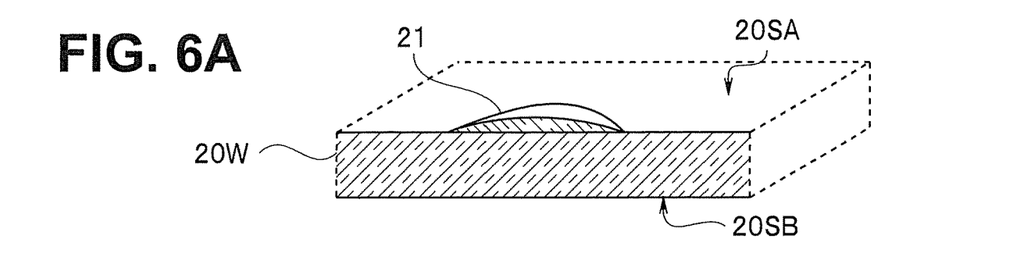
FIG. 6A is a perspective cross-sectional view for describing the method for manufacturing the optical unit for endoscope according to the first embodiment.

For example, as illustrated in FIG. 6A, in the glass wafer 20W, a plurality of resin lenses 21 is disposed at predetermined positions in a first principal surface 20SA. The position of disposition of each resin lens 21 is located inside an area in which a recess portion T20 is to be formed in a subsequent step (inside a recess portion formation area) (see FIG. 6B). Each resin lens 21 is disposed by, for example, applying a transparent resin for lens, pressing a mold having a predetermined shape against the transparent resin for lens and applying ultraviolet (UV) light from below (second principal surface 20SB side) to cure the transparent resin for lens.

On the other hand, e.g., a plurality of light receiving sections 41 are formed at predetermined positions on a semiconductor wafer 40W of, e.g., silicon by a known semiconductor manufacturing technique.

<Step S12> Recess Portion Formation

Figure 6B:
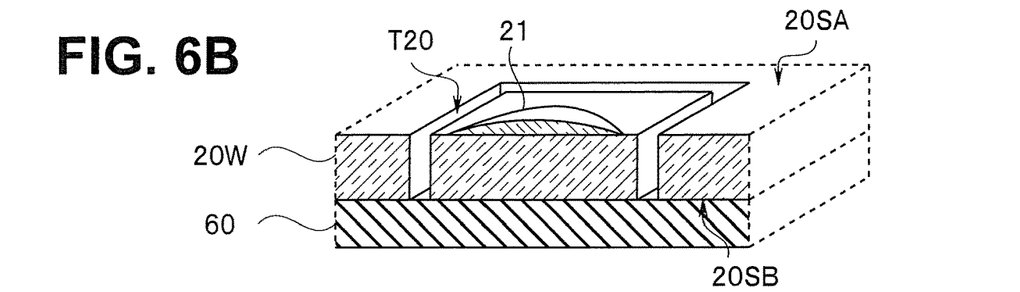
FIG. 6B is a perspective cross-sectional view for describing the method for manufacturing the optical unit for endoscope according to the first embodiment.

As illustrated in FIG. 6B, a holding wafer 60, which is a support wafer, is disposed on a second principal surface 20SB of the glass wafer 20W, and the respective annular recess portions T20 are formed so as to surround the plurality of resin lenses 21. Each recess portion T20 is an annular through glass hole (TGH) extending through the glass wafer 20W. The recess portions T20 are formed by means of, e.g., wet etching or dry etching with an etching mask (not illustrated) disposed on the first principal surface 20SA of the glass wafer 20W.

A plurality of recess portions are formed in a matrix at respective same positions in the glass wafers 10W to 30W.

<Step S13> Light Shielding Wall Formation

Figure 6C:
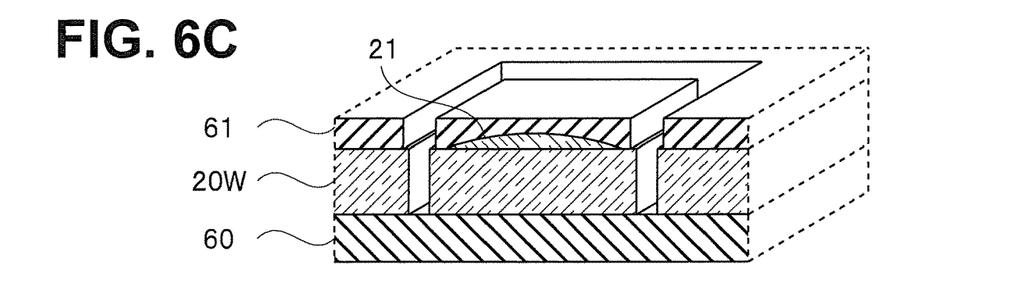
FIG. 6C is a perspective cross-sectional view for describing the method for manufacturing the optical unit for endoscope according to the first embodiment.

A light shielding material is charged in the recess portions T20 to fabricate light shielding walls 25. In the image pickup unit 1 according to the present embodiment, the light shielding walls 25 are formed by means of electric plating using copper.

In other words, as illustrated in FIG. 6C, an underlaying conductive film is disposed on the glass wafer 20W by means of, for example, CVD, and then, a plating mask 61 is disposed, and a copper plating film is disposed inside each recess portion T20 by means of electric plating.

A thickness of each light shielding wall 25, that is, a width of an opening of each recess portion is preferably no less than 10 μm, particularly preferably no less than 30 μm from the perspective of light shielding and productivity. An upper limit for the thickness of each light shielding wall 25 is, for example, 200 μm from the perspective of thinning.

If the opening of each recess portion is, for example, no less than 50 μm, it is not necessary that the inside of the recess portion be fully filled with the light shielding material (plating film). Each recess portion may have space inside as long as at least a wall surface on the inner side of the recess portion is covered by a plating film having a thickness that is equal to or larger than a predetermined thickness (for example, no less than 10 μm).

Also, the light shielding material may be provided by charging a light shielding resin, for example, a resin in which carbon particles are dispersed in the recess portions and curing the resin. However, from the perspective of light shielding property and productivity, the light shielding material is preferably a metal such as Ni, Cu, Au, Sn, SnAg or In, particularly preferably an electric plating film.

Figure 6D:
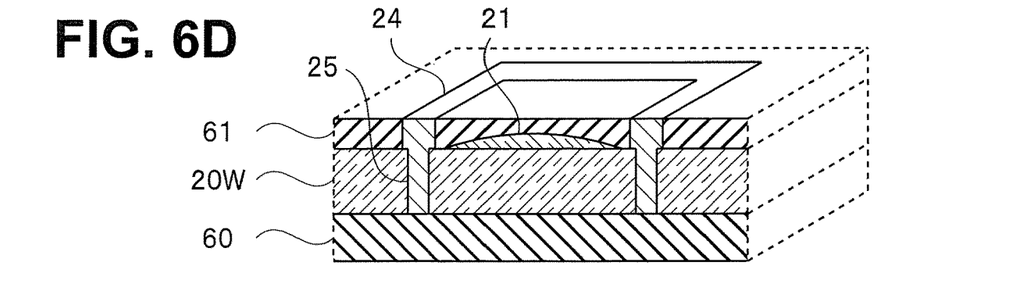
FIG. 6D is a perspective cross-sectional view for describing the method for manufacturing the optical unit for endoscope according to the first embodiment.

In the image pickup unit 1 according to the present embodiment, a Cu plating film forming a light shielding wall 25 is provided so as not only to extend inside the relevant recess portion T20 but also to extend in a projecting manner from the first principal surface 20SA. In other words, the annular projection portion 24 provided so as to extend from the light shielding wall 25 is disposed simultaneously with disposition of the light shielding wall 25 and includes a material that is the same as the material of the light shielding wall 25.

Here, the light shielding wall 25 and the projection portion 24 may be made of different materials. For example, it is possible that the light shielding wall 25 is made of Cu and the projection portion 24, of gold. It is also possible that only an upper part of the projection portion is made of gold.

Figure 6E:
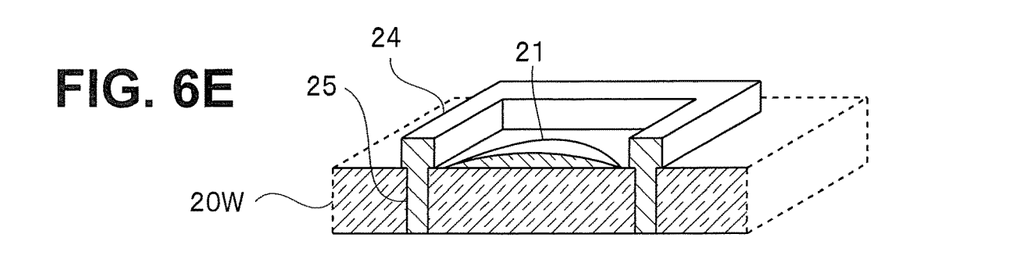
FIG. 6E is a perspective cross-sectional view for describing the method for manufacturing the optical unit for endoscope according to the first embodiment.

Then, the holding wafer 60 is removed, and the glass wafer 20W with the plurality of resin lenses 21 disposed inside the respective frame-like projection portions 24 is thus completed.

As described later, the annular projection portions 24 having a function as a light shielding wall each also serve as a spacer defining a distance between the relevant glass wafer (optical element) and a glass wafer (optical element) adjacent to the glass wafer when the glass wafers are stacked.

Likewise, light shielding walls 15, 35 and projection portions 14, 34 are disposed in respective glass wafers 10W, 30W. As illustrated in FIG. 2, each projection portion 14 of the back face 10SB of the glass wafer 10W has not only a spacer function but also a function of a diaphragm portion configured to limit an amount of light on the optical path.

Also, annular projection portions 44 surrounding the respective light receiving sections 41 are formed in an image pickup surface 40SA of the semiconductor wafer 40W.

<Step S14> Wafer Bonding

Figure 8:
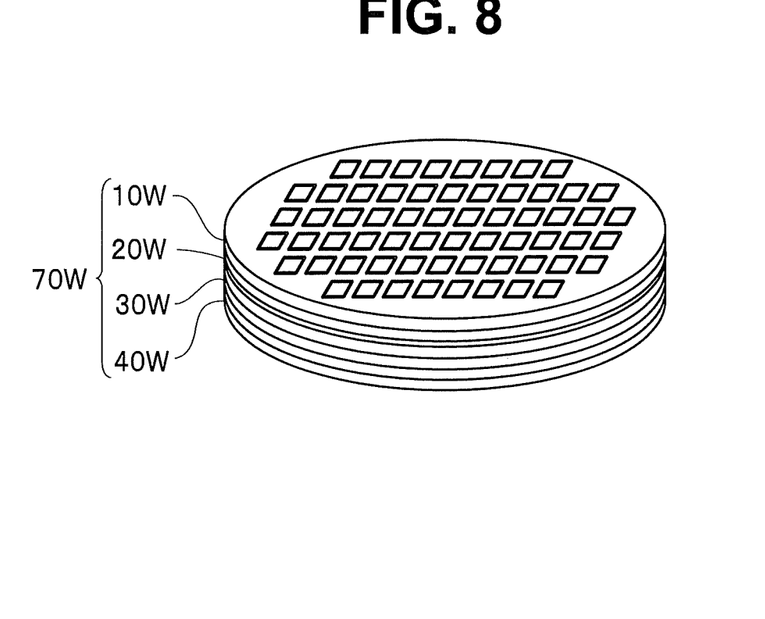
FIG. 8 is a perspective view of a bonded wafer for describing the method for manufacturing the optical unit for endoscope according to the first embodiment.

As illustrated in FIG. 8, a bonded wafer 70W is fabricated by stacking the plurality of glass wafers 10W to 30W with the respective light shielding walls fabricated and the image pickup wafer 40W including a plurality of image pickup devices.

In other words, for example, positioning is performed so that the projection portions of each wafer are brought into contact with openings of the light shielding walls of another wafer, and the wafer and the other wafer are then bonded to each other. For the bonding, an adhesive may be used, but it is preferably to use, e.g., metal bonding without using an adhesive. A sealing resin 50 is charged in an outer peripheral portion of each annular bonding part for reinforcement.

Also, a bonded wafer in which bonding surfaces each are formed of gold facilitates metal bonding using ultrasound bonding or room-temperature bonding. A wafer in which upper portions of projection portions are made of, e.g., Sn, which is a low-melting-point metal, enables metal bonding by means of heating.

<Step S15> Cutting

Figure 9:
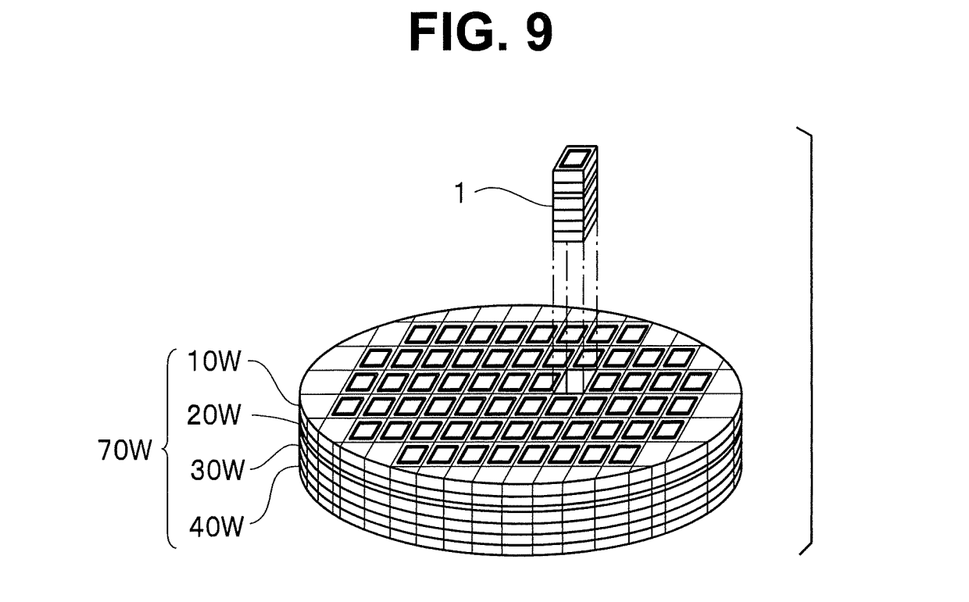
FIG. 9 is a perspective view for describing the method for manufacturing the optical unit for endoscope according to the first embodiment.

As illustrated in FIG. 9, the bonded wafer 70W is cut into individual image pickup units 1.

According to the image pickup unit manufacturing method according to the present embodiment, an optical unit for endoscope 1, the optical unit having a light shielding function, can easily be manufactured.

<Modifications>

Next, modifications of the optical unit for endoscope according to the first embodiment will be described. An optical unit for endoscope according to each of the modifications is similar to the image pickup unit 1 or the lens unit 2 and has a function that is the same as the function of the image pickup unit 1 or the lens unit 2, and thus, components each having a function that is the same as a function of a component in the image pickup unit 1 or the lens unit 2 are provided with reference numerals that are the same as the reference numerals of the component and description of such components will be omitted.

<Modification 1>

Figure 10:
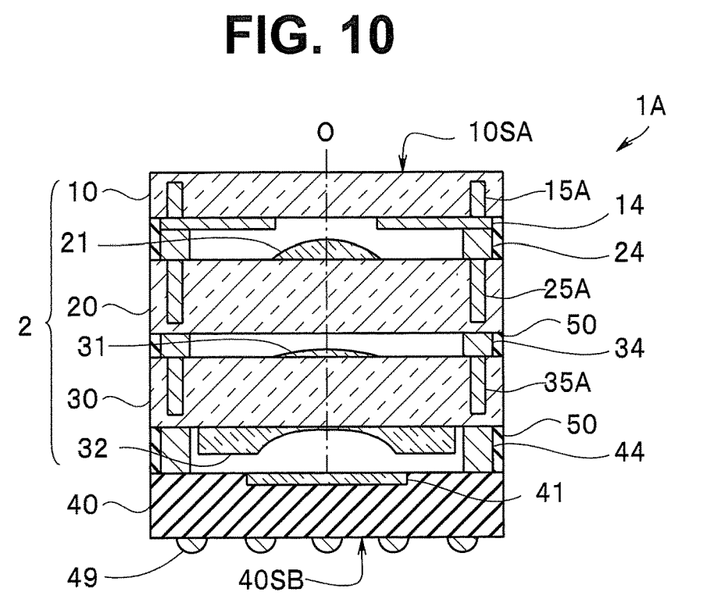
FIG. 10 is a cross-sectional view of an optical unit for endoscope according to modification 1 of the first embodiment.

As illustrated in FIG. 10, in an image pickup unit 1A (lens unit 2A) according to modification 1, heights of light shielding walls 15A, 25A, 35A, that is, depths of respective recess portions are 80% of respective thicknesses of optical elements 10, 20, 30, and the recess portions are not through vias but bottomed vias.

In the case of the image pickup unit 1A, annular recess portions formed in wafers are not through holes, and as opposed to the image pickup unit 1 illustrated in FIG. 6B, when the recess portions are formed, it is not necessary to dispose a holding wafer 60 on a second principal surface 20SB of a glass wafer 20W.

Therefore, the image pickup unit 1A and the lens unit 2A are easier to manufacture.

From the perspective of light shielding capability, it is preferable that the depths of the recess portions (heights of the light shielding walls) be no less than 75% of the thicknesses of the respective optical elements 10, 20, 30.

Also, from the perspective of light-shielding capability, if the depth of a recess portion is smaller than the thickness of the relevant optical element by 50 μm, a width of the relevant light shielding wall is preferably no less than 50 μm, particularly preferably no less than 100 μm.

Also, it is possible that the recess portion of at least any one of the optical elements 10, 20, 30 is bottomed and the recess portions of the other optical elements are annular through holes.

<Modification 2>

Figure 11A:
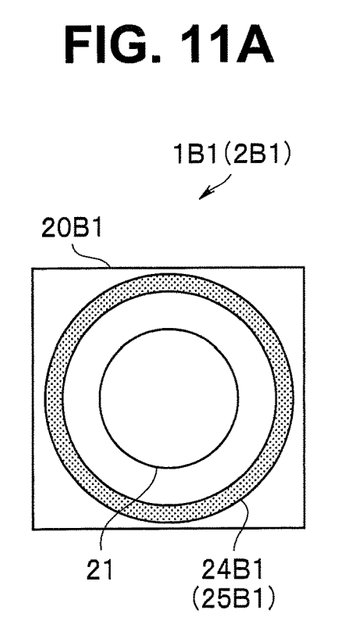
FIG. 11A is a top view of an optical element in an optical unit for endoscope according to modification 2 of the first embodiment.
Figure 11B:
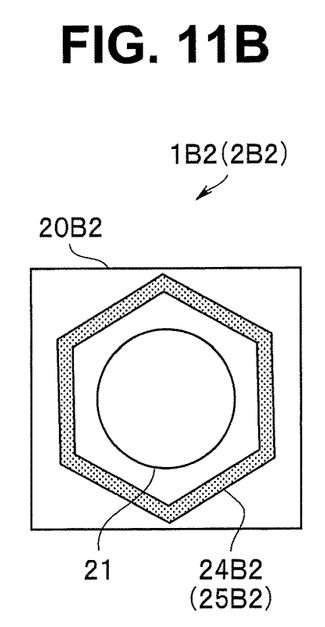
FIG. 11B is a top view of an optical element in the optical unit for endoscope according to modification 2 of the first embodiment.

In the image pickup unit 1 (lens unit 2), an outer periphery of the light shielding wall 15, etc., has a rectangular frame shape in a cross-section. On the other hand, a light shielding wall 25B1, etc., in an image pickup unit 1B1 (lens unit 2B1) according to the modification illustrated in FIG. 11A has a round shape in a cross-section. Also, a light shielding wall 25B2, etc., in an image pickup unit 1B2 (lens unit 2B2) according to the modification illustrated in FIG. 11B has a hexagonal shape in a cross-section. In other words, a shape of each light shielding wall may be a round shape or a polygonal shape as long as the light shielding wall surrounds an optical path.

Figure 11C:
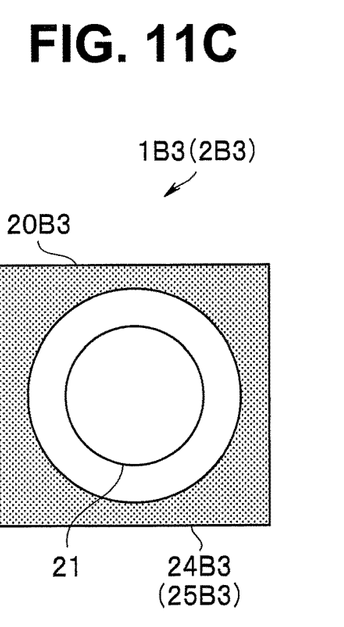
FIG. 11C is a top view of an optical element in the optical unit for endoscope according to modification 2 of the first embodiment.

Also, as in a light shielding wall 25B3 of an image pickup unit 1B3 (lens unit 2B3) according to the modification illustrated in FIG. 11C, an outer periphery of a light shielding wall may be wide as long as a center space surrounds an optical path.

Also, light shielding walls of optical elements 10, 20, 30 may have different shapes.

<Modification 3>

Figure 12:
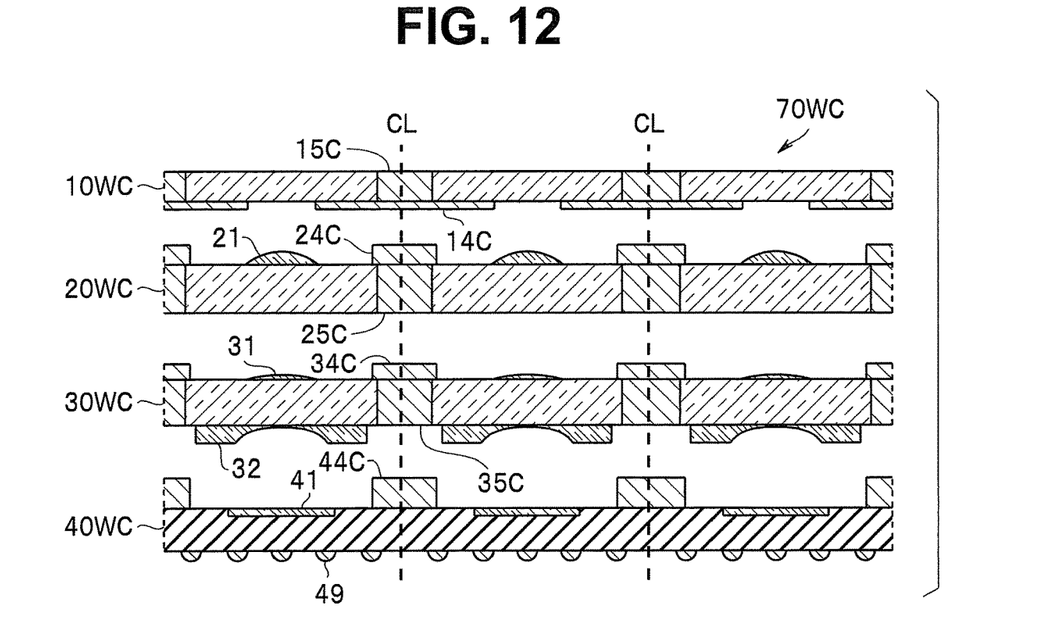
FIG. 12 is an exploded cross-sectional view of a bonded wafer in an optical unit for endoscope according to modification 3 of the first embodiment.
Figure 13:
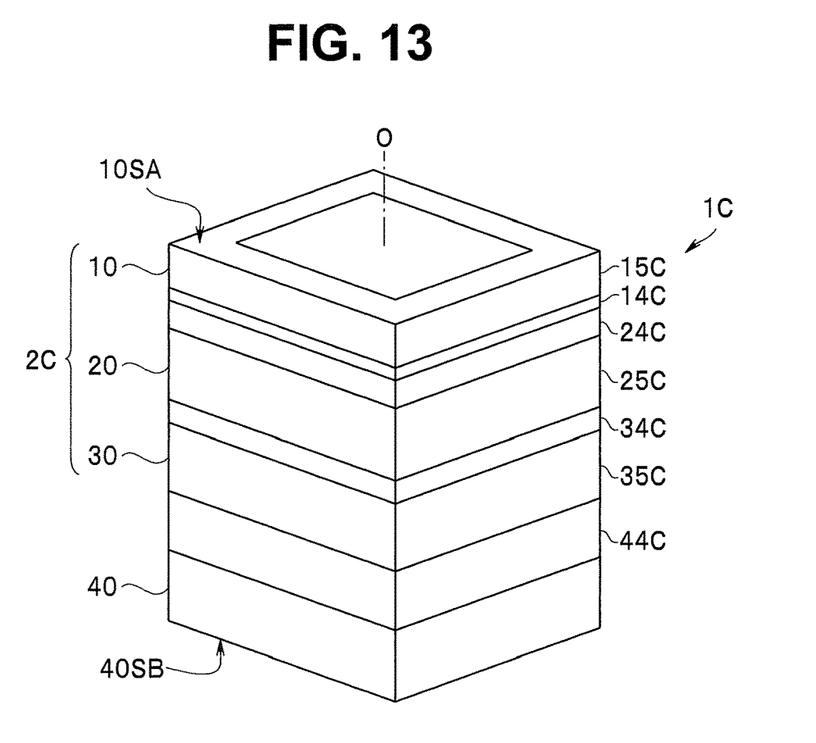
FIG. 13 is a perspective view of the optical unit for endoscope according to modification 3 of the first embodiment.

In the case of an optical unit for endoscope (an image pickup unit 1C or a lens unit 2C) according to modification 3, as illustrated in FIG. 12, a plurality of recess portions formed in an element wafer 10WC, etc., extend across respective cutting lines CL. Therefore, in the image pickup unit 1C obtained as a result of a bonded wafer 70WC being cut into individual pieces, as illustrated in FIG. 13, the annular recess portions, an outer periphery of each of the recess portions having a rectangular shape, in the bonded wafer 70WC are cutout portions in side faces, and a light shielding wall 15C, etc., and a spacer 14C, etc., are exposed in the side faces. In other words, respective outer faces of the light shielding wall 15C, etc., and the spacer 14C, etc., are cutting surfaces.

The image pickup unit 1C can easily be thinned in comparison with the image pickup unit 1, etc. Also, a width of an opening of each recess portion in the image pickup unit 1C is larger than the width of the opening in the image pickup unit 1, etc., and thus, a light shielding material, for example, a plating film can easily be charged in the recess portion.

Also, it should be understood that as with the image pickup unit 1A, the image pickup unit 1C also provides effects that are the same as the effects of the image pickup unit 1A by forming each recess portion as a bottomed via.

Second Embodiment

An image pickup unit 1D according to a second embodiment is similar to the image pickup unit 1 or the lens unit 2 and has a function that is the same as the function of the image pickup unit 1 or the lens unit 2, and thus, components each having a function that is the same as a function of a component in the image pickup unit 1 or the lens unit 2 are provided with reference numerals that are the same as the reference numerals of the components in the image pickup unit 1 or the lens unit 2 and description of such components will be omitted.

Figure 5:
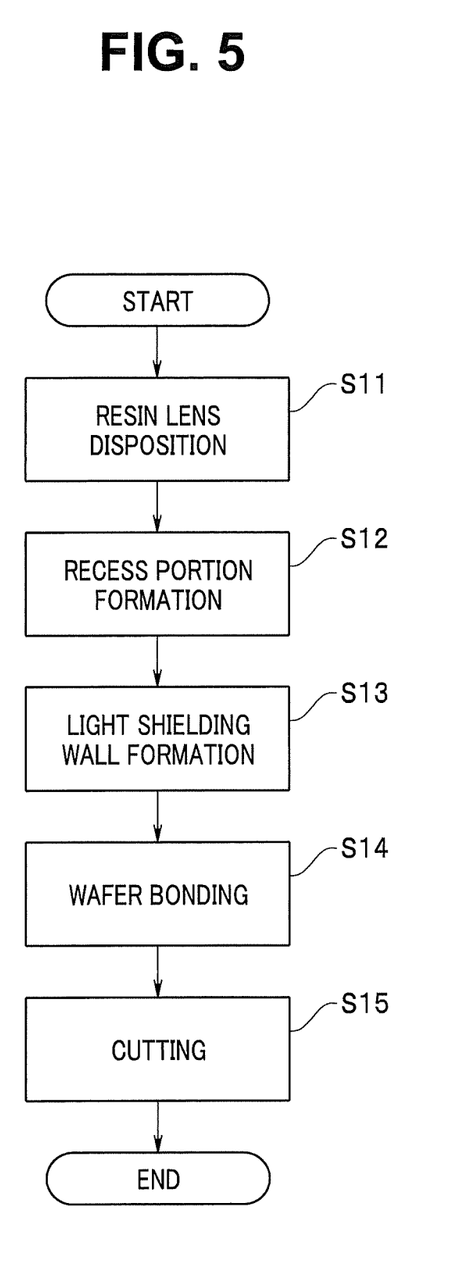
FIG. 5 is a flowchart of a method for manufacturing the optical unit for endoscope according to the first embodiment.
Figure 14:
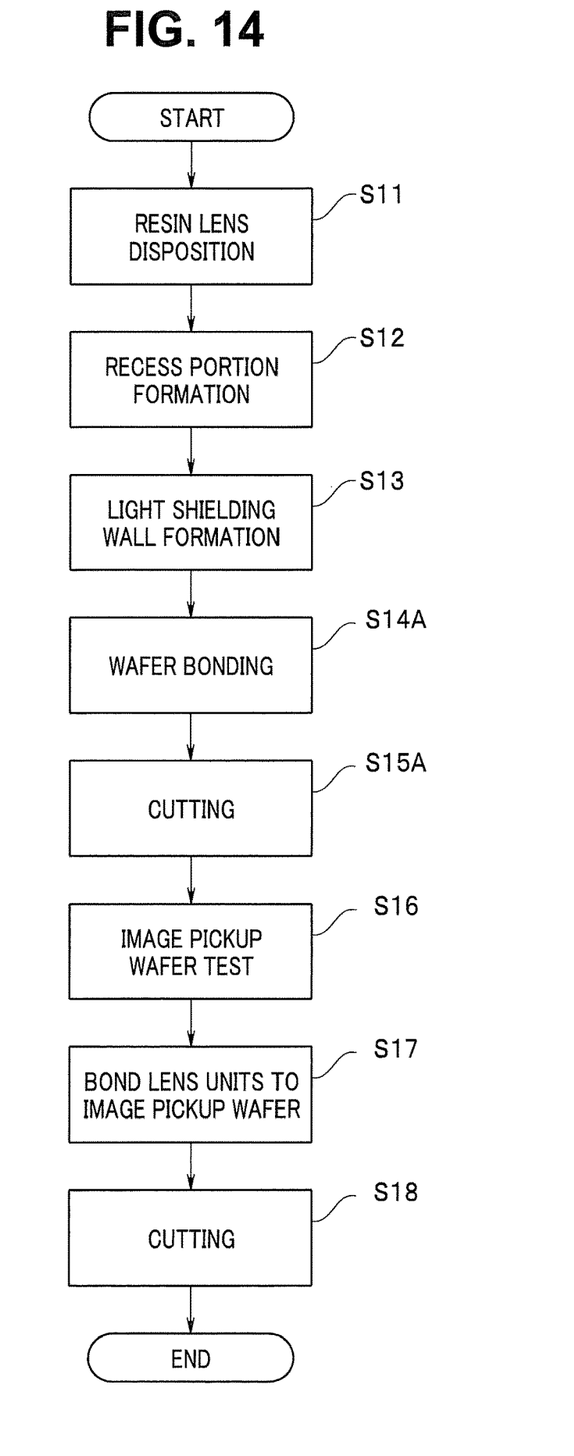
FIG. 14 is a flowchart of a method for manufacturing an optical unit for endoscope according to a second embodiment.

As in the flowchart illustrated in FIG. 14, a method for manufacturing the image pickup unit 1D is similar to the method for manufacturing the image pickup unit 1 illustrated in FIG. 5. However, in a wafer bonding step (S14A), an image pickup wafer 40W is not bonded.

Thus, what is fabricated in a step of cutting a bonded wafer (step 15A) are rectangular lens units 2D each including no image pickup device.

Figure 15:
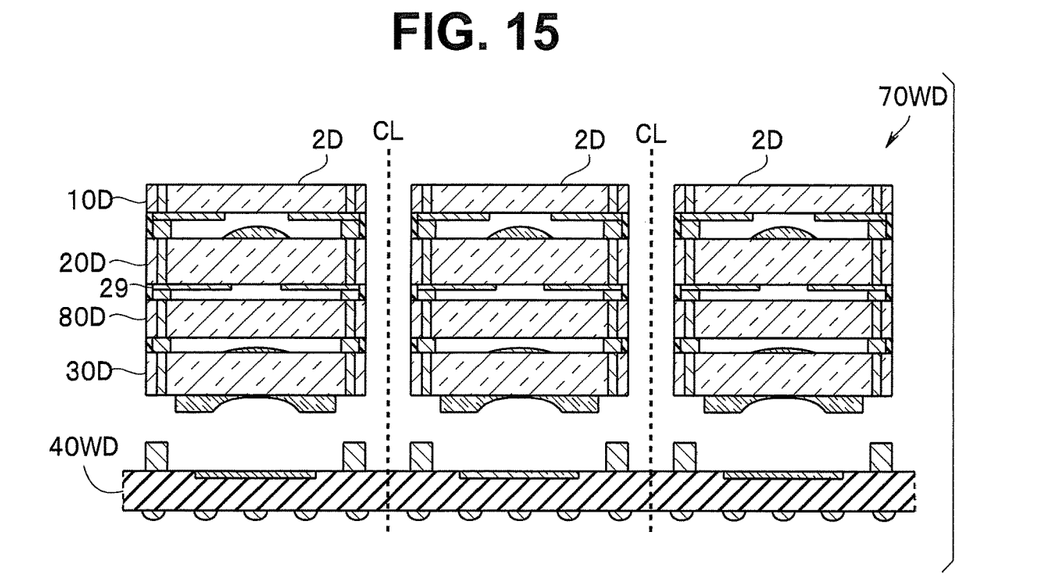
FIG. 15 is an exploded cross-sectional view of a bonded wafer in the optical unit for endoscope according to the second embodiment.
Figure 16:
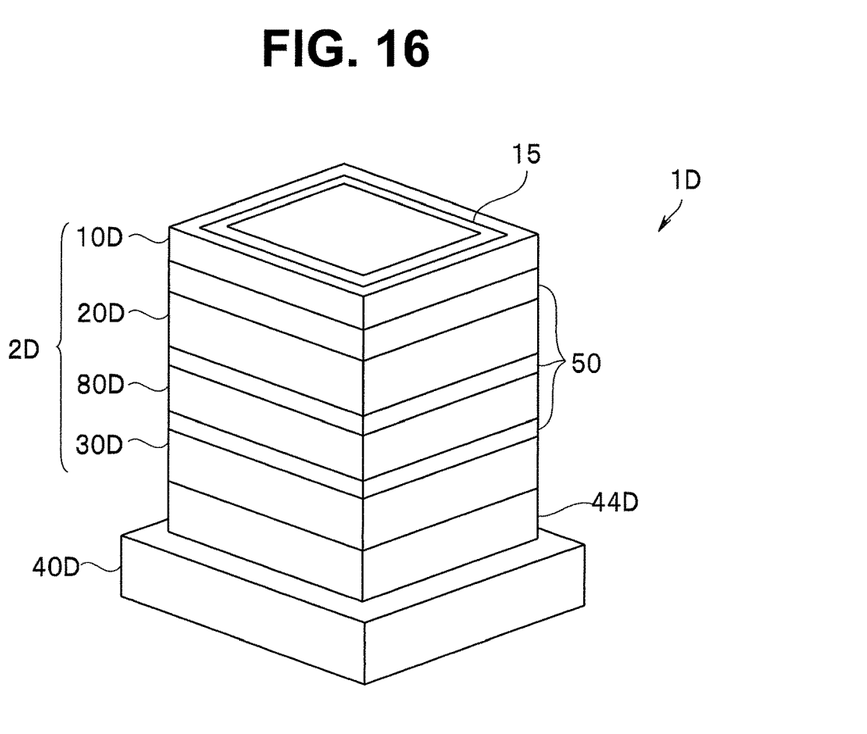
FIG. 16 is a perspective view of the optical unit for endoscope according to the second embodiment.

In other words, as illustrated in FIG. 15, the lens units 2D each include optical elements 10D, 20D, 80D, 30D. In each lens unit 2D, the optical element 30D is a cover glass element, and the optical element 80D is an infrared cut filter element. A spacer 29 having a diaphragm function is disposed also on the optical element 20D.

In other words, the number, the type and the stacking order of optical elements and arrangement of a filter, etc., included in a lens unit are changed according to the specifications.

On the other hand, after forming light receiving sections 41, etc., on the image pickup wafer 40WD, the image pickup wafer 40WD is subjected to an operation test (step S16) in the wafer state.

Then, the lens unit 2D is disposed on only each of image pickup devices determined as non-defective products in the test from among a plurality of image pickup devices included in the image pickup wafer 40WD (step S17). The image pickup units 1D obtained as a result of the image pickup wafer 40WD being cut into individual pieces (step S18) each include an image pickup device 40D determined as a non-defective product in the operation test, and thus the yield of the manufacture is good.

Here, in the step of cutting a bonded wafer (step 15A), it is possible that the bonded wafer is cut into lens blocks each including a plurality of lens units and the lens blocks are disposed on the image pickup wafer 40WD. Conversely, it is possible that the image pickup wafer 40WD is cut into image pickup blocks each including a plurality of image pickup devices and the lens units 2 are then disposed on the image pickup blocks. Furthermore, it is possible that image pickup devices obtained as a result of the image pickup wafer being cut into individual pieces is disposed on the bonded wafer including the plurality of lens units.

It should be understood that an endoscope including any of the image pickup unit 1A (lens unit 2A), the image pickup unit 1B1 (lens unit 2B1), the image pickup unit 1B2 (lens unit 2B2) and the image pickup unit 1D in a rigid distal end portion 9A of an insertion portion 9B has the effects of the endoscope 9 and further has the effects of the relevant image pickup unit (lens unit).

The present invention is not limited to the above-described embodiments and the like, and various changes, combinations and applications are possible without departing from the spirit of the invention.

What is claimed is:

1. An optical unit for endoscope, the optical unit comprising:
   a plurality of optical elements stacked, each of the plurality of optical elements including a glass substrate as a base, the glass substrates having a same size in respective cross-sections in a direction orthogonal to an optical path, wherein
   at least one of the optical elements is a lens element including a resin lens disposed on the base; and
   each of the plurality of optical elements includes an annular recess surrounding the optical path and extending through the glass substrate, and a light shielding wall made of a light shielding material disposed in the recess;
   further comprising annular projection portions each including a light shielding material and being provided so as to extend from the respective light shielding walls, each of the projection portions is a spacer, configured to define a distance between two adjacent optical elements of the optical elements;
   wherein the light shielding walls and the corresponding spacer are made of a same material; and
   each of the light shielding walls and the corresponding spacer are made of an electric plating film.

2. The optical unit for endo scope according to claim 1, wherein at least one of the spacers is configured so as to have a function of a diaphragm configured to block a part of the optical path to adjust an amount of light.

3. The optical unit for endoscope according to claim 1, further comprising an image sensor including a light receiving section configured to receive light collected by the plurality of optical elements.

4. The optical unit for endoscope according to claim 3, wherein a cross-section, in the direction orthogonal to the optical path, of the image sensor has a size that is same as the size of the cross-sections, in the direction orthogonal to the optical path, of the glass substrates.

5. An endoscope comprising:
   an insertion portion having a rigid distal end portion; and
   the optical unit according to claim 1 disposed in the rigid distal end portion.

\* \* \* \* \*